(12) United States Patent
Cals-Grierson et al.

(10) Patent No.: US 7,008,630 B2
(45) Date of Patent: Mar. 7, 2006

(54) LIPOCHROMAN-6 AS NO-SYNTHASE INHIBITOR AND USES

(75) Inventors: Marie-Madeleine Cals-Grierson, Meudon (FR); Pascale Pelletier, Anthony (FR)

(73) Assignee: L' Oreal, Paris (FR)

( * ) Notice: Subject to any disclaimer, the term of this patent is extended or adjusted under 35 U.S.C. 154(b) by 95 days.

(21) Appl. No.: 10/258,812

(22) PCT Filed: Apr. 27, 2001

(86) PCT No.: PCT/FR01/01317

§ 371 (c)(1),
(2), (4) Date: Mar. 3, 2003

(87) PCT Pub. No.: WO01/82888

PCT Pub. Date: Nov. 8, 2001

(65) Prior Publication Data

US 2003/0165444 A1    Sep. 4, 2003

(30) Foreign Application Priority Data

Apr. 28, 2000  (FR)  .................................. 00 05520

(51) Int. Cl.
*A61K 7/00*        (2006.01)

(52) U.S. Cl. ....................................... 424/401; 424/400
(58) Field of Classification Search ................ 424/400, 424/401
See application file for complete search history.

(56) References Cited

U.S. PATENT DOCUMENTS 5,449,688 A * 9/1995 Wahl et al. .................. 514/546

FOREIGN PATENT DOCUMENTS

| DE | 197 11 565 | 8/1998 |
| EP | 0 445 735 | 9/1991 |
| EP | 0 655 239 | 5/1995 |
| EP | 1 002 533 | 5/2000 |
| FR | 2 740 339 | 4/1997 |

OTHER PUBLICATIONS

S. Yenes et al., *Tetrahedron Letters*, Vo. 55, No. 49, Dec. 3, 1999, pp. 14111-14122.

* cited by examiner

*Primary Examiner*—Shelley A. Dodson
(74) *Attorney, Agent, or Firm*—Buchanan Ingersoll, P.C.

(57) ABSTRACT

The invention concerns relates to the use of an efficient amount of lipochroman-6, in a physiologically acceptable medium, in a composition or for preparing a composition, the lipochroman-6 or the composition being designed to inhibit NO-synthase.

27 Claims, No Drawings

LIPOCHROMAN-6 AS NO-SYNTHASE INHIBITOR AND USES

The present invention relates to the use of an effective amount of lipochroman-6, in a physiologically acceptable medium, in a composition or for preparing a composition, the lipochroman-6 or the composition being intended to inhibit NO-synthase.

The term "NO-synthase" covers a family of enzymes which carry out the enzymatic catalysis of L-arginine to citrulline, during which catalysis a gaseous medium with multiple functions, nitric oxide, or NO, is produced.

NO-synthases exist in three forms, two constitutive forms, nomenclature including neuronal NO-synthase (or NOS 1) and endothelial NO-synthase (or NOS 3), and the inducible form (or NOS 2) (Medecine/Sciences, 1992, 8, pp. 843–845). It is understood elsewhere in the text that, unless otherwise indicated, the term "NO-synthase" covers all the isoforms of the enzyme.

Thus, according to the invention, the term, "NO-synthase inhibitors" is intended to mean any product which, ultimately, notwithstanding the NO-synthase isoform, leads to a decrease in the concentration of NO. Mention may be made, by way of example, of products which reduce the amount of active NO-synthase, which block the enzymatic activity of NO-synthase or its induction, or which inhibit the activity of the NO produced.

By virtue of its structure, nitric oxide has an additional electron which makes it extremely chemically reactive. It is of note that such compounds are harmful, and the intention is to limit the production thereof as much as possible. Thus, in the case of nitric oxide, NO-synthase inhibitors have been widely studied.

NO is a multifunctional signal molecule which is active in a large variety of systems and of tissues of the body. Besides its damaging effects for cells, which are linked to its hyperreactivity due to its structure comprising an additional electron, it is acknowledged, inter alia, as being particularly involved in the cardiovascular system (regulator of blood pressure with vasodilator effect, inhibitor of platelet aggregation with anticlotting effect), in the nervous system (memory, modulation of neurotransmitter release), and in the immune system (modulation of immune defenses, inflammation, involvement in autoimmune pathological conditions).

It is now well accepted that NO plays a predominant role in the skin. NO can be synthesized by all the varieties of cells which make up the skin and, therefore, it is involved in multiple and complex processes of regulation, such as regulation of cellular differentiation and/or proliferation, of vasodilation, of melanogenesis, or of the response to environmental variations (homeostasis).

Its involvement in cellular differentiation and proliferation (stimulatory effect), particularly of keratinocytes, associates it both with growth of the epidermis and cicatrization and with hyperproliferative disorders (psoriasis).

Due to its electron hyperreactivity possibly leading to degradation, or even destruction, of cells, NO is involved in apoptotic processes and in intrinsic and/or extrinsic aging of the skin. It is involved in immunological and inflammatory processes of the skin. It is in fact commonly accepted that NO plays a role in contact hypersensitivity reactions, in allergic manifestations of the skin, and in the immune response of the skin. Similarly, besides its direct pro-inflammatory role, it is the mediator between neuropeptides such as substance P and/or the calcitonin gene-related peptide (CGRP) in neurogenic inflammatory processes of the skin, hence its involvement in the phenomena of "sensitive" skin.

The involvement of NO in vasodilation means that it is associated with erythemas of the skin, particularly erythemas induced by ultraviolet radiation, localized or diffuse erythematous eruptions of the skin, such as those caused by drugs, toxins and/or viral or bacterial infections, and with acne rosacea.

NO is acknowledged to be an intermediate in the melanogenesis induced by ultraviolet radiation type B (UVB). It is also thought to be one of the factors involved in disorders of the hypermelanosis type.

NO also appears to be involved in the control of sweating and also in that of lipolysis (inhibitory effect), or in hair loss.

Finally, NO is known to have an influence on the barrier function of the skin and therefore on the moisturization thereof (inhibitory effect).

The advantage which exists in having NO-synthase inhibitors can therefore be understood.

In this regard, many inhibitors have already been proposed in the prior art. Mention may be made more particularly of $N^G$-monomethyl-L-arginine (NMMA), $N^G$-nitro-L-arginine methyl ester (NAME), $N^G$-nitro-L-arginine (NNA), $N^G$-amino-L-arginine (NAA), $N^G,N^G$-dimethylarginine (asymmetric dimethylarginine, called ADMA), diphenyleneiodonium chloride, 2-(4-carboxyphenyl)-4,4,5,5-tetramethylimidazoline-1-oxy 3-oxide, 7-nitroindazole, N(5)-(1-iminoethyl)-L-ornithine, aminoguanidine, canavanine and ebselen.

Without casting doubt on the effectiveness of these products, it is noted that they are chemical compounds which may induce problems, or even harmful side effects, in users, who generally prefer using natural products.

The aim of the present invention is to provide a novel NO-synthase inhibitor which is also a natural NO-synthase inhibitor.

Surprisingly and unexpectedly, the applicant has demonstrated that lipochroman-6 has the property of being an NO-synthase inhibitor, particularly an inhibitor of inducible NO synthase (NOS 2), which makes it a good candidate for uses in applications in which it proves to be advantageous to use an NO-synthase inhibitor, particularly in cosmetics.

Lipochroman-6 is a compound corresponding to the general formula:

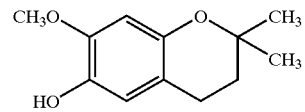

This compound is described in the prior art as an antioxidant, as a free-radical scavenger, as an inhibitor of lipid peroxidation and as an agent protecting cells against peroxynitrite-induced damage. However, it is not described as an NO-synthase inhibitor.

The first subject of the invention is therefore the use of an effective amount of lipochroman-6, in a physiologically acceptable medium, in a composition or for preparing a composition, the lipochroman-6 or the composition being intended to inhibit NO-synthase.

The expression "physiologically acceptable medium" is understood to mean a medium compatible with the skin, the mucous membranes, the nails and the hair.

The second subject of the invention is the use of an effective amount of lipochroman-6, in a physiologically acceptable medium, in a composition or for preparing a composition, the lipochroman-6 or the composition being intended for use in all domains in which inhibition of NO-synthases proves to be necessary, particularly in the domain of the skin and/or of the hair.

Lipochroman-6, or the composition containing it, may be used to slow down or even inhibit cellular differentiation and/or proliferation, and/or vasodilation, and/or melanogenesis, and/or the response to environmental variations (homeostasis).

Thus, the third subject of the invention is the use of an effective amount of lipochroman-6, in a physiologically acceptable medium, in a composition or for preparing a composition, the lipochroman-6 or the composition being intended to slow down or even inhibit cellular differentiation and/or proliferation, particularly to regulate growth of the epidermis and/or to treat hyperproliferative disorders such as, for example, psoriasis.

The fourth subject of the invention is the use of an effective amount of lipochroman-6, in a physiologically acceptable medium, in a composition or for preparing a composition, the lipochroman-6 or the composition being intended to inhibit degradation and/or destruction of cells and to inhibit apoptotic processes, particularly of skin cells, very particularly of keratinocytes, and/or to treat intrinsic and/or extrinsic aging of cells, particularly of skin cells.

The fifth subject of the invention is the use of an effective amount of lipochroman-6, in a physiologically acceptable medium, in a composition or for preparing a composition, the lipochroman-6 or the composition being intended to inhibit or even suppress the immunological and/or inflammatory processes related to NO synthesis, such as for example contact hypersensitivity reactions and/or allergic manifestations and/or the immune response, particularly of the skin.

The lipochroman-6 or the composition is articularly intended to decrease or even inhibit inflammation of the skin, particularly neurogenic inflammatory processes of the skin, and therefore to treat "sensitive" skin.

The sixth subject of the invention is the use of an effective amount of lipochroman-6, in a physiologically acceptable medium, in a composition or for preparing a composition, the lipochroman-6 or the composition being intended to treat acne rosacea and/or erythemas of the skin, particularly erythemas induced by ultraviolet radiation and/or localized or diffuse erythematous eruptions of the skin, such as those caused by drugs, toxins and/or viral or bacterial infections.

The seventh subject of the invention is the use of an effective amount of lipochroman-6, in a physiologically acceptable medium, in a composition or for preparing a composition, the lipochroman-6 or the composition being intended to inhibit melanogenesis induced by ultraviolet radiation type A and/or B, and/or to treat disorders of the hypermelanosis type.

The eighth subject of the invention is the use of an effective amount of lipochroman-6, in a physiologically acceptable medium, in a composition or for preparing a composition, the lipochroman-6 or the composition being intended to control sweating and/or to stimulate lipolysis and/or to inhibit hair loss and/or to reinforce the barrier function of the skin and/or to stimulate moisturization of the skin.

According to the invention, the composition comprising the lipochroman-6 may be a cosmetic or dermatological composition. Preferentially according to the invention, the composition is a cosmetic composition.

Preferentially according to the invention, the lipochroman-6 or the composition comprising it is applied to the skin topically.

According to the invention, the amount of lipochroman-6 extract used in the composition depends, of course, on the desired effect and may therefore vary within a wide range.

To give an order of magnitude, according to the invention, the lipochroman-6 may be used in an amount representing from $10^{-4}$% to 20% of the total weight of the composition, and preferentially in an amount representing from $5 \times 10^{-3}$% to 10% of the total weight of the composition.

Of course, according to the invention, the lipochroman-6 may be combined with other NO-synthase inhibitors, for instance plant extracts, such as, for example, an extract of at least one plant of the species *Olea europaea* or an extract of Ginkgo biloba or an extract of *Vitis vinifera* or an extract of green tea or of cacao.

The ninth subject of the invention is a method of cosmetic treatment for the purpose of treating disorders related to NO synthesis, characterized in that a cosmetic composition comprising at least lipochroman-6, in a physiologically acceptable medium, is used by application to the skin, to the hair and/or to the mucous membranes.

The method of cosmetic treatment of the invention is aimed at improving the appearance of the individual suffering from disorders due to NO synthesis.

The method of cosmetic treatment of the invention may in particular be used by applying the cosmetic compositions as defined above, according to the normal technique for using these composition. Thus, for example, it is possible to apply creams, gels, sera, lotions, make-up-removing milks or antisun compositions to the skin or to dry hair, to apply a hair lotion to wet hair or to apply shampoos, or to apply dentifrice to the gums.

Whatever the form of the composition according to the invention in which the lipochroman-6 is used, it may be ingested, injected or applied to the skin (to any area of body skin), the hair, the nails or the mucous membranes (oral, jugal, gingival, genital or conjunctival membranes). Depending on the method of administration, the composition according to the invention may be in any pharmaceutical form normally used.

For a topical application to the skin, the composition may in particular be in the form of an aqueous or oily solution or of a dispersion of the lotion or serum type, of emulsions of liquid or semi-liquid consistency of the milk type, obtained by dispersing a fatty phase in an aqueous phase (O/W emulsion) or conversely (W/O emulsion), or of suspensions or emulsions of soft consistency of the aqueous or anhydrous cream or gel type, or alternatively of microcapsules or microparticles, or of vesicular dispersions of ionic and/or nonionic type. These compositions are prepared according to the usual methods.

They may also be used for the hair in the form of aqueous, alcoholic or aqueous-alcoholic solutions, or in the form of creams, of gels, of emulsions or of foams, or alternatively in the form of aerosol compositions also comprising a pressurized propellant.

For injection, the composition may be in the form of an aqueous or oily lotion or in the form of serum. For the eyes, it may be in the form of drops and, for ingestion, it may be in the form of capsules, of granules, of syrups or of tablets.

The amounts of the various constituents of the compositions according to the invention are those conventionally used in the domains under consideration.

These compositions in particular constitute cleansing, protective, treating or care creams for the face, for the hands, for the feet, for the major anatomical folds or for the body (for example day creams, night creams, make-up removing creams, foundation creams and antisun creams), fluid foundations, make-up-removing milks, protective body milks or bodycare milks, antisun milks, skincare lotions, gels or mousses, for instance cleansing lotions, antisun lotions, artificial tanning lotions, bath compositions, deodorant compositions comprising a bactericidal agent, aftershave gels or lotions, hair-removing creams, insect-repellent compositions, pain-relief compositions, compositions for treating certain diseases of the skin, such as eczema, acne rosacea, psoriasis, lichens and severe pruritis.

The compositions according to the invention may also consist of solid preparations constituting cleansing soaps or bars.

The compositions may also be packaged in the form of an aerosol composition also comprising a pressurized propellant.

The composition according to the invention may also be a haircare composition, and especially a shampoo, a setting lotion, a treating lotion, a styling cream or gel, a dye composition (especially for oxidation dyeing) optionally in the form of coloring shampoos, restructuring lotions for the hair, a permanent-waving composition (in particular a composition for the first stage of a permanent-waving operation), a lotion or a gel for preventing hair loss, an antiparasitic shampoo, etc.

The composition may also be for orodental use, for example a toothpaste. In this case, the composition may contain adjuvants and additives which are usual for compositions for oral use and, in particular, surfactants, thickeners, wetting agents, polishing agents such as silica, various active ingredients such as fluorides, in particular sodium fluoride, and optionally sweeteners such as sodium saccharinate.

When the composition is an emulsion, the proportion of the fatty phase may range from 5% to 80% by weight, and preferably from 5% to 50% by weight, relative to the total weight of the composition. The oils, waxes, emulsifiers and co-emulsifiers used in the composition in emulsion form are chosen from those conventionally used in cosmetics. The emulsifier and co-emulsifier are present, in the composition, in an amount ranging from 0.3% to 30% by weight, and preferably from 0.5 to 20% by weight, relative to the total weight of the composition. The emulsion may also contain lipid vesicles.

When the composition is an oily solution or gel, the fatty phase may represent more than 90% of the total weight of the composition.

In a known manner, the cosmetic composition may also contain adjuvants that are common in cosmetics, such as hydrophilic or lipophilic gelling agents, hydrophilic or lipophilic additives, preserving agents, antioxidants, solvents, fragrances, fillers, screening agents, odor absorbers and dyestuffs. The amounts of these various adjuvants are those conventionally used in cosmetics and, for example, from 0.01% to 10% of the total weight of the composition. Depending on their nature, these adjuvants may be introduced into the fatty phase, into the aqueous phase and/or into the lipid spherules.

As oils or waxes which may be used in the invention, mention may be made of mineral oils (liquid petroleum jelly), plant oils (liquid fraction of karite butter or sunflower oil), animal oils (perhydrosqualene), synthetic oils (Purcellin oil), silicone oils or waxes (cyclomethicone) and fluoro oils (perfluoropolyethers), beeswax, carnauba wax or paraffin wax. Fatty alcohols or fatty acids (stearic acid) may be added to these oils.

As emulsifiers which may be used in the invention, mention may be made, for example, of glyceryl stearate, polysorbate 60 and the mixture of PEG-6/PEG-32/glycol stearate sold under the name Tefose® 63 by the company Gattefosse.

As solvents which may be used in the invention, mention may be made of lower alcohols, in particular ethanol and isopropanol, and propylene glycol.

As hydrophilic gelling agents which may be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums and clays, and, as lipophilic gelling agents, mention may be made of modified clays, such as bentones, metal salts of fatty acids, such as aluminum stearates, and hydrophobic silica, ethylcellulose and polyethylene.

The composition may contain other hydrophilic active agents, such as proteins or protein hydrolyzates, amino acids, polyols, urea, allantoin, sugars and sugar derivatives, water-soluble vitamins, plant extracts and hydroxy acids.

Lipophilic active agents which may be used include retinol (vitamin A) and derivatives thereof, tocopherol (vitamin E) and derivatives thereof, essential fatty acids, ceramides, essential oils, and salicylic acid and derivatives thereof.

According to the invention, the composition may combine at least one lipochroman-6 extract with other active agents in particular intended to prevent and/or treat skin ailments. Among these active agents, mention may be made, by way of example, of:

agents for modifying differentiation and/or proliferation and/or pigmentation of the skin, such as retinoic acid and isomers thereof, retinol and esters thereof, vitamin D and derivatives thereof, kojic acid or hydroquinone;

antibacterial agents, such as clindamycin phosphate or erythromycin or antibiotics of the tetracyclin family;

antiparasitic agents, in particular metronidazole, crotamiton or pyrethrinoids;

antifungal agents, in particular compounds belonging to the imidazole family, such as econazole, ketoconazole or miconazole, or salts thereof, polyene compounds, such as amphotericin B, compounds of the allylamine family, such as terbinafine, or alternatively octopirox;

nonsteroidal antiinflammatory agents, such as ibuprofen and salts thereof, diclofenac and salts thereof, acetylsalicylic acid, acetaminophen or glycyrrhetinic acid;

anesthetics, such as lidocaine hydrochloride and derivatives thereof;

antipruriginous agents, such as thenaldine, trimeprazine or cyproheptadine;

keratolytic agents, such as alpha- and beta-hydroxycarboxylic acids or beta-keto carboxylic acids, their salts, amides or esters and more particularly hydroxy acids such as glycolic acid, lactic acid, salicylic acid, citric acid and fruit acids in general, and 5-n-octanoylsalicylic acid;

free-radical scavengers, such a alpha-tocopherol or esters thereof, superoxide dismutases, certain metal chelating agents, or ascorbic acid and esters thereof;

antiseborrheic agents, such as progesterone;

antidandruff agents, such as octopirox or zinc pyrithione;

antiacne agents, such as retinoic acid or benzoyl peroxide;

plant extracts or extracts of microbial origin;

peptides and derivatives thereof, such as, for example, the tripeptide Lys-Pro-Val.

The following examples and compositions illustrate the invention without in any way limiting it. In the compositions, the proportions given are percentages by weight.

EXAMPLE 1

Biological Activity of lipochroman-6

The activity of lipochroman-6 on inducible NO-synthase was evaluated in the test described by Heck et al. (J. B. C., Vol. 267, No. 30, 21277–21280, Oct. 25, 1992).

The aim of this test is to demonstrate the decrease in nitrate and nitrite concentration, ultimately, after stimulation of NO-synthase 2.

The following controls were introduced into the tests:
A: positive control (induction of the enzyme): mixtures of γ-interferon (1 000 U/ml) and interleukin-1β (100 U/ml);
B: negative control (maximum inhibition): $N^G$-monomethyl-L-arginine (L form) at 200 $\mu$M;
C: control for specificity of inhibition: $N^G$-monomethyl-L-arginine (D form) at 200 $\mu$M.

In order to determine the activity of the product to be tested, the amount of stable NO reaction products (nitrites and nitrates) is measured using the nitric calorimetric assay kit sold by the company Boehringer under the reference 1756.28.

The lipochroman-6 was tested at the concentrations of 0.005% and 0.01% (weight/volume) in ethanol.

| Product tested | % inhibition |
| --- | --- |
| A | 0 |
| B | 100 |
| C | 0 |
| Lipochroman-6: 0.005% | 38 |
| Lipochroman-6: 0.01% | 95 |

Lipochroman-6 has an inhibitory effect on inducible NO-synthase.

EXAMPLE 2

Examples of formulations illustrating the invention. These compositions were obtained by simply mixing the various components.

Composition 1: Gel for the face

| | |
| --- | --- |
| Lipochroman-6 | 0.1% |
| Methylparaben | 0.2% |
| Carbomer | 0.7% |
| Polyethylene glycol (8OE) | 10.0% |
| Imidazolidinyl urea | 0.3% |
| Triethanolamine | 0.58% |
| Water | qs for 100% |

Composition 2: Lotion

| | |
| --- | --- |
| Lipochroman-6 | 2.00% |
| Antioxidant | 0.05% |
| Isopropanol | 40.00% |
| Preserving agent | 0.30% |
| Water | qs for 100% |

Composition 3: Care gel

| | |
| --- | --- |
| Lipochroman-6 | 3.00% |
| Hydroxypropylcellulose* | 1.00% |
| Antioxidant | 0.05% |
| Isopropanol | 40.00% |
| Preserving agent | 0.30% |
| Water | qs for 100% |

Composition 4: Care cream (oil-in-water emulsion)

| | |
| --- | --- |
| Lipochroman-6 | 5.00% |
| Glyceryl stearate | 2.00% |
| Polysorbate 60** | 1.00% |
| Stearic acid | 1.40% |
| Triethanolamine | 0.70% |
| Carbomer | 0.40% |
| Liquid fraction of karite butter | 12.00% |
| Perhydrosqualene | 12.00% |
| Antioxidant | 0.05% |
| Fragrance | 0.50% |
| Preserving agent | 0.30% |
| Water | qs for 100% |

Composition 5: Shampoo

| | |
| --- | --- |
| Lipochroman-6 | 0.50% |
| Hydroxypropylcellulose* | 1.00% |
| Fragrance | 0.50% |
| Preserving agent | 0.30% |
| Water | qs for 100% |

Composition 6: Care cream (oil/water emulsion)

| | |
| --- | --- |
| Lipochroman-6 | 5.00% |
| Glyceryl stearate | 2.00% |
| Polysorbate 60** | 1.00% |
| Stearic acid | 1.40% |
| 5-n-octanoylsalicylic acid | 0.50% |
| Triethanolamine | 0.70% |
| Carbomer | 0.40% |
| Liquid fraction of karite butter | 12.00% |
| Perhydrosqualene | 12.00% |
| Antioxidant | 0.05% |
| Fragrance | 0.50% |
| Preserving agent | 0.30% |
| Water | qs for 100% |

Composition 7: Pain-relieving gel

| | |
| --- | --- |
| Lipochroman-6 | 5.00% |
| Hydroxypropylcellulose* | 1.00% |
| Antioxidant | 0.05% |
| Lidocaine hydrochloride | 2.00% |
| Isopropanol | 40.00% |
| Preserving agent | 0.30% |
| Water | qs for 100% |

Composition 8: Care cream for sunburn (oil-in-water emulsion)

| | |
| --- | --- |
| Lipochroman-6 | 5.00% |
| Glyceryl stearate | 2.00% |
| Polysorbate 60** | 1.00% |
| Stearic acid | 1.40% |
| Glycyrrhetinic acid | 2.00% |
| Triethanolamine | 0.70% |
| Carbomer | 0.40% |
| Liquid fraction of karite butter | 12.00% |
| Sunflower oil | 10.00% |
| Antioxidant | 0.05% |
| Fragrance | 0.50% |
| Preserving agent | 0.30% |
| Water | qs for 100% |

Composition 9: Gel for treating acne

| | |
| --- | --- |
| Lipochroman-6 | 5.00% |
| All-trans retinoic acid | 0.05 |
| Hydroxypropylcellulose* | 1.00% |
| Antioxidant | 0.05% |
| Isopropanol | 40.00% |
| Preserving agent | 0.30% |

-continued

| | |
|---|---|
| Water | qs for 100% |

Composition 10: Lotion for eliminating scars due to acne

| | |
|---|---|
| Lipochroman-6 | 3.00% |
| Glycolic acid | 50.00% |
| Hydroxypropylcellulose* | 0.05% |
| Preserving agent | 0.30% |
| NaOH | qs for pH = 2.8% |
| Ethanol | qs for 100% |

*Klucel H ® sold by the company Hercules
**Tween 60 ® sold by the company ICI

EXAMPLE 3

Effect of Composition 1 of Example 2 on Sensitive Skin

It has been demonstrated that sensitive skin is characterized by very strong neurosensory reactivity of the skin to topical application, on the face, of capsaicin (Magnusson and Koskinen, Acta Derm. Venereol. (Stockh), 1996, 76, 129–132).

An itching sensation is one of the most predictive signs of sensitive skin.

The composition of example 2 was therefore tested on a population (15 volunteers) of individuals exhibiting the characteristics of sensitive skin, in comparison to the same composition containing no lipochroman-6.

The composition and the control are applied to the face at the angle of the cheeks, in a random and double-blind manner.

30 minutes after treatment, a cream containing 0.075% of capsaicin is applied to the treated areas.

The itching sensation is then evaluated according to:
0=none
1=slight
2=moderate
3=strong The mean results are given in the following table:

| Time (min) | Control | Composition 1 |
|---|---|---|
| 15 | 1.00 | 0.93 |
| 20 | 0.93 | 0.87 |
| 25 | 0.80 | 0.60 |

The gel containing lipochroman-6 has a protective effect against the itching sensation induced by capsaicin.

The invention claimed is:

1. A method for the cosmetic treatment of a disorder having NO synthesis as a causative factor, said method comprising applying to the skin, to the hair and/or to the mucous membranes of an individual in need thereof, an NO-synthase inhibiting amount of lipochroman-6 in a physiologically acceptable medium.

2. A method for inhibiting NO-synthase in a subject in need of same, said method comprising administering to said subject a composition comprising an effective NO-synthase inhibiting amount of lipochroman-6 in a physiologically acceptable medium.

3. The method as claimed in claim 2, for inhibiting or suppressing immunological and/or inflammatory processes.

4. The method as claimed in claim 3, for treating contact hypersensitivity reactions and/or allergic manifestations and/or the immune response.

5. The method as claimed in claim 3, for decreasing or inhibiting inflammation of the skin.

6. The method as claimed in claim 5, for treating neurogenic inflammatory processes of the skin.

7. The method as claimed in claim 2, for treating "sensitive" skin.

8. The method as claimed in claim 2, wherein the lipochroman-6 is in an amount representing from $10^{-4}$% to 20% of the total weight of the composition.

9. The method as claimed in claim 8, wherein the lipochroman-6 is in an amount representing from $5 \times 10^{-3}$% to 10% of the total weight of the composition.

10. A method for inhibiting NO-synthase in a subject in need of same other than a subject having an immunological and/or inflammatory condition, said method comprising administering to said subject a composition comprising an effective NO-synthase inhibiting amount of lipochroman-6 in a physiologically acceptable medium.

11. The method as claimed in claim 10, wherein the lipochroman-6 is in an amount representing from $10^{-4}$% to 20% of the total weight of the composition.

12. The method as claimed in claim 11, wherein the lipochroman-6 is in an amount representing from $5 \times 10^{-3}$% to 10% of the total weight of the composition.

13. The method as claimed in claim 10, for slowing down or inhibiting cellular differentiation and/or proliferation.

14. The method as claimed in claim 10, for slowing down or inhibiting growth of the epidermis and/or treating hyperproliferative disorders.

15. The method as claimed in claim 10, for inhibiting degradation and/or destruction of cells.

16. The method as claimed in claim 10, for inhibiting cellular apoptotic processes.

17. The method as claimed in claim 10, for treating intrinsic and/or extrinsic aging.

18. The method as claimed in claim 10, for treating erythemas.

19. The method as claimed in claim 18, for treating erythemas induced by ultraviolet radiation.

20. The method as claimed in claim 10, for treating localized or diffuse erythematous eruptions of the skin.

21. The method as claimed in claim 10, for treating acne rosacea.

22. The method as claimed in claim 10, for inhibiting melanogenesis induced by ultraviolet radiation, and/or to treat hypermelanosis.

23. The method as claimed in claim 10, for controlling sweating.

24. The method as claimed in claim 10, for stimulating lipolysis.

25. The method as claimed in claim 10, for inhibiting hair loss.

26. The method as claimed in claim 10, for reinforcing the barrier function of the skin.

27. The method as claimed in claim 10, for stimulating moisturization of the skin.

* * * * *